United States Patent [19]

Jones et al.

[11] Patent Number: 4,634,802

[45] Date of Patent: Jan. 6, 1987

[54] HYDROCARBON DEHYDROGENATION

[75] Inventors: C. Andrew Jones, Newtown Square; John A. Sofranko, Malvern, both of Pa.

[73] Assignee: Atlantic Richfield Company, Los Angeles, Calif.

[21] Appl. No.: 745,726

[22] Filed: Jun. 17, 1985

Related U.S. Application Data

[63] Continuation-in-part of Ser. No. 600,655, Apr. 16, 1984, abandoned, which is a continuation-in-part of Ser. No. 522,937, Aug. 12, 1983, Pat. No. 4,499,322, which is a continuation-in-part of Ser. No. 522,936, Aug. 12, 1983, Pat. No. 4,495,374, and a continuation-in-part of Ser. No. 683,118, Dec. 18, 1984.

[51] Int. Cl.$^4$ ............................................. C07C 5/333
[52] U.S. Cl. .................................. 585/656; 585/658; 585/659; 585/661
[58] Field of Search ............... 585/654, 656, 658, 659, 585/661

[56] References Cited

U.S. PATENT DOCUMENTS

| | | | |
|---|---|---|---|
| 3,410,920 | 11/1968 | Olson | 585/656 |
| 3,682,838 | 8/1972 | Bloch | 585/656 |
| 3,845,156 | 10/1974 | Farha | 585/658 |
| 4,310,717 | 1/1982 | Eastman et al. | 585/661 |
| 4,368,346 | 1/1983 | Eastman | 585/658 |
| 4,454,363 | 6/1984 | Teng et al. | 585/435 |

Primary Examiner—William R. Dixon, Jr.
Assistant Examiner—Cynthia A. Prezlock
Attorney, Agent, or Firm—Craig E. Larson

[57] ABSTRACT

An improved method for dehydrogenating dehydrogenatable hydrocarbons by contacting a gas comprising said hydrocarbons and an oxidative dehydrogenation agent at dehydrogenation conditions, the improvement which comprises contacting the hydrocarbon with an oxidative dehydrogenation agent containing a promoting amount of alkali metal and/or compounds thereof and associated with a support selected from the group consisting of alkaline earth metals and compounds thereof.

24 Claims, No Drawings

HYDROCARBON DEHYDROGENATION

CROSS REFERENCE TO RELATED APPLICATIONS

This application is a continuation-in-part of U.S. Patent Application Ser. No. 600,655 filed Apr. 16, 1984, and now abandoned which in turn is a continuation-in-part of U.S. Patent Application Ser. Nos. 522,937 now U.S. Pat. No. 4,499,322 and 522,936, now U.S. Pat. No. 4,495,374 both filed Aug. 12, 1983. This application is also a continuation-in-part of U.S. Pat. Application Ser. No. 683,118, filed Dec. 18, 1984, the entire content of which is incorporated herein by reference.

BACKGROUND OF THE INVENTION

This invention relates to dehydrogenation of dehydrogenatable hydrocarbons. This invention more particularly relates to oxidative dehydrogenation processes.

SUMMARY OF THE INVENTION

It has now been found that dehydrogenation of dehydrogenatable hydrocarbons is improved by contacting a gas comprising said hydrocarbon at dehydrogenation conditions with a solid which comprises:

(a) at least one reducible oxide of at least one metal which oxides when contacted with hydrocarbons at said temperature are reduced and produce dehydrogenated hydrocarbon products and water;
(b) at least one promoter selected from the group consisting of alkali metals and compounds thereof; and
(c) a support comprising at least one member of the group consisting of alkaline earth metals and compounds thereof.

Preferably component (a) comprises at least one reducible oxide of at least one reducible oxide of at least one metal selected from the group consisting of Mn, Sn, In, Ge, Pb, Sb and Bi. Component (a) is preferably present in an amount within the range of about 1 to 40 wt.% based on the combined weight of the component (a) metal (e.g., Mn) and the support, more preferably within the range of about 5 to 30 wt.%, still more preferably within the range of about 10 to 20 wt.%. Alkali metals are selected from the group consisting of Li, Na, K, Rb and Cs. Preferred promoters are Na, K and Li. Sodium is a particularly preferred promoter. Particularly preferred reducible metal oxides are reducible oxides of manganese. Alkaline earth metals are selected from the group consisting of Mg, Ca, Sr and Ba. Magnesia is a particularly preferred support.

The stability of the promoted oxidative dehydrogenation agent may be enhanced by incorporating a stabilizing amount of phosphorus into the composition. However, the agent is effective in the absence of phosphorus.

DETAILED DESCRIPTION OF THE INVENTION

Oxidative dehydrogenation agents comprise at least one oxide of at least one metal, which oxides when contacted with dehydrogenatable hydrocarbons at dehydrogenation conditions (e.g., at a temperature selected within the range of about 500° to 1000° C.) produce dehydrogenated hydrocarbon products, coproduct water, and a reduced metal oxide. The composition thus contains at least one reducible oxide of at least one metal. The term "reducible" is used to identify those oxides of metal which are reduced by contacting hydrocarbon at dehydrogenation conditions (e.g., at temperatures selected within the range of about 500°–1000° C.). The term "oxide(s) of metal(s)" includes: (1) one or more metal oxides (i.e., compounds described by the general formula $M_xO_y$ wherein M is a metal and the subscripts $x$ and $y$ designate the relative atomic proportions of metal and oxygen in the composition) and/or (2) one or more oxygen-containing metal compounds, provided that such oxides and compounds have the capability of performing to produce dehydrogenated hydrocarbon products as set forth herein.

Preferred oxidative dehydrogenation agents comprise reducible oxides of metals selected from the group consisting of Mn, Sn, In, Ge, Sb, Pb, and Bi and mixtures thereof. Particularly preferred oxidative dehydrogenation agents comprise a reducible oxide of manganese and mixtures of a reducible oxide of manganese with other oxidative dehydrogenation agents.

The promoted oxidative dehydrogenation agent of this invention contains, in addition to the foregoing elements, at least one alkali metal. The atomic ratio in which these materials are combined to form the dehydrogenation agent is not narrowly critical. However, the preferred atomic ratio of the reducible oxide component (expressed as the metal, e.g., Mn) to the alkali metal component (expressed as the metal, e.g., Na) is within the range of about 0.1–100:1, more preferably within the range of about 0.3–10:1.

The promoted oxidative dehydrogenation agent may also contain at least one phosphorus component. The amount of the phosphorus component contained in the dehydrogenation agent is again not narrowly critical. The atomic ratio of phosphorus to the reducible oxide component (expressed as the metal, e.g., Mn) is preferably less than about 2:1. More preferably this ratio is within the range of about 0.1–0.5:1.

A preferred oxidative dehydrogenation agent used in the process of this invention may be further expressed by the following empirical formula:

$$A_aB_bP_cO_d$$

wherein A is selected from the group consisting of Mn, Sn, In, Ge, Pb, Sb, Bi and mixtures thereof; B is selected from the group consisting of alkali metals including mixtures thereof; a to d indicate the atomic ratio of each component; and when a is 10, b is within the range of about 1–33, c is within the range of about 0–20, and d has a value which is determined by the valence and proportions of the other elements present. These components may be associated with a support material as described below.

The promoted oxidative dehydrogenation agent of this invention is associated with a support comprising at least one member of the group consisting alkaline earth metals and compounds thereof. Preferred support materials comprise MgO, CaO, BaO and mixtures thereof. MgO is a particularly preferred support.

The promoted oxidative dehydrogenation agent can be prepared by any suitable method. Conventional methods such as precipitation, co-precipitation, impregnation, or dry mixing can be used. Supported solids may be prepared by methods such as adsorption, impregnation, precipitation, co-precipitation, and dry-mixing. Thus, a compound of Mn, Sn, In, Ge, Pb, Sb and/or Bi; a compound of an alkali metal; and optionally a compound of phosphorus can be combined in any suitable way. When phosphorus is incorporated in the agent, it is desirable to provide it in the form of a phosphate of an alkali metal. Substantially any compound of these elements can be employed in the preparation of the promoted dehydrogenation agent.

A suitable method of preparation is to impregnate a support with solutions of compounds of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried in an oven to remove solvent and the dried solid is prepared for use by calcining, preferably in air at a temperature selected within the range of about 300° to 1200° C. Particular calcination temperatures will vary depending upon the particular metal compound or compounds employed.

If phosphorus is used, the alkali metal and phosphorus are preferably added to the composition as compounds containing both P and alkali metals. Examples are the orthophosphates, metaphosphates, and pyrophosphates of alkali metals. Pyrophosphates have been found to give desirable results. Sodium pyrophosphate is particularly preferred. The alkali metal and the phosphorus can be incorporated into the promoted dehydrogenation agent as separate compounds. Suitable phosphorus compounds useful for preparing the compositions include orthophosphoric acid, ammonium phosphates and ammonium hydrogenphosphates.

Regardless of how the components are combined, the resulting composite generally will be dried and calcined at elevated temperatures prior to use in the process of this invention.

One class of preferred compositions is characterized by the substantial absence of catalytically effective Ni and the noble metals (e.g., Rh, Pd, Ag, Os, Ir, Pt and Au) and compounds thereof, to minimize the deleterious catalytic effects of such metals and compounds thereof. For example, at the conditions (e.g., temperatures) under which the present compositions are used, these metals tend to promote coke formation and oxides of these metals tend to promote formation of combustion products ($CO_x$) rather than the desired hydrocarbons. The term "catalytically effective" is used to identify that quantity of one or more of nickel and the noble metals and compounds thereof which, when present, substantially changes the distribution of products obtained when employing the compositions of this invention.

The dehydrogenatable hydrocarbon feedstock employed in the method of this invention is intended to include a wide variety of hydrocarbons: e.g., $C_2+$ alkanes, cycloalkanes, olefins, alkylaromatic, etc. The dehydrogenated product will of course depend in part on the feed stock selected. For example, alkanes may be dehydrogenated to form olefins, diolefins, alkynes, etc., and olefins may be dehydrogenated to form diolefins, alkynes, etc. Thus, potential uses for the present process include the following conversions:
(1) ethane→ethylene→acetylene;
(2) propane→propylene;
(3) butane→butene→butadiene;
(4) 2-methylbutane→2-methylbutenes→isoprene; and
(5) toluene→stilbene.
One preferred class of feedstocks comprises $C_2$–$C_5$ alkanes.

Operating temperatures for the contacting of hydrocarbon-containing gas and the promoted oxidative dehydrogenation agent are selected within the range of about 500° to 1000° C., the particular temperature selected depending upon the particular reducible metal oxide(s) employed. For example, reducible oxides of certain metals may require operating temperatures below the upper part of the recited range to minimize sublimation or volatilization of the metals (or compounds thereof) during hydrocarbon contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the hydrocarbon contacting step are not critical to the presently claimed invention. Contacting dehydrogenatable hydrocarbons and a promoted oxidative dehydrogenation agent to form dehydrogenated hydrocarbons also produces a reduced metal oxide and co-product water. The exact nature of the reduced metals oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the promoted oxidative synthesizing agent.

In carrying out the present process, a single reactor apparatus containing a fixed bed of solids may be used with intermittent or pulsed flow of a first gas comprising hydrocarbon and a second gas comprising oxygen (e.g., oxygen, oxygen diluted with an inert gas, or air, preferably air). The hydrocarbon contacting step and the oxygen contacting step may also be performed in physically separate zones with solids recirculating between the two zones.

Thus, a suitable method for dehydrogenating dehydrogenatable hydrocarbons comprises: (a) contacting a gas comprising said hydrocarbon and particles comprising a promoted oxidative dehydrogenation agent to form dehydrogenated hydrocarbon products, co-product water, and reduced metal oxide; (b) removing particles comprising reduced metal oxide from the first zone and contacting the reduced particles in a second zone with an oxygen-containing gas to form particles comprising a promoted oxidative dehydrogenation agent; and (c) returning the particles produced in the second zone to the first zone. The steps are preferably repeated at least periodically, and more preferably the steps are continuous. In the more preferred embodiment solids are continuously circulated between at least one hydrocarbon-contact zone and at least one oxygen contact zone.

Particles comprising a promoted oxidative dehydrogenation agent which are contacted with hydrocarbon may be maintained as fluidized, ebullating, or entrained beds of solids. Preferably hydrocarbon is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In the more preferred embodiment of the present invention, hydrocarbon feedstock and particles comprising a promoted oxidative dehydrogenation agent are continuously introduced into a hydrocarbon contact zone maintained at dehydrogenation conditions. Dehydrogenation conditions include the temperatures and pressures described above. Gaseous reaction products from the hydrocarbon contact zone (separated from entrained solids) are further processed—e.g., they are passed through a fractionating system wherein the desired hydrocarbon products are separated from unconverted hydrocarbon and combustion products. Unconverted hydrocarbon may be recovered and recycled to the hydrocarbon contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the methane contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material deposited on the particles. At least a portion of the particles comprising promoted oxidative synthesizing agent which are produced in the oxygen contact zone are returned to the hydrocarbon contact zone.

The rate of solids withdrawal from the hydrocarbon contact zone is desirably balanced with the rate of solids passing from the oxygen contact zone to the hydrocarbon contact zone so as to maintain a substantially constant inventory of particles in the hydrocarbon contact zone, thereby enabling steady state operation of dehydrogenation synthesizing system.

What is claimed is:

1. A method for dehydrogenating alkanes to form the corresponding olefins which comprises contacting a gas comprising said alkanes at a temperature within the range of about 500° to 850° C. with a solid comprising:
   (a) at least one reducible oxide of Ge,
   (b) at least one promoter selected from the group consisting of alkali metals and compounds therefore, and
   (c) a support comprising at least one member of the group consisting of oxides of alkaline earth metals.

2. The method of claim 1 wherein component (c) is magnesia.

3. The method of claim 1 wherein the promoter is selected from the group consisting of sodium, sodium compounds and mixtures thereof.

4. The method of claim 1 wherein the promoter is selected from the group consisting of potassium, potassium compounds and mixtures thereof.

5. The method of claim 1 wherein the promoter is selected from the group consisting of lithium, lithium compounds and mixtures thereof.

6. The method of claim 1 wherein the solid contains a stabilizing amount of phosphorus.

7. The method of claim 1 wherein the gas comprising alkanes and the solid comprising at least one reducible oxide of Ge are contacted in a first zone to form olefins corresponding to said alkanes, coproduct water, and solids comprising a reduced oxide of Ge; said olefins are recovered; said solids comprising a reduced oxide of Ge are at least periodically contacted with an oxygen-containing gas in a second zone to produce a solid comprising a reducible oxide of Ge; and returning said solid comprising a reducible oxide of Ge from the second zone to the first zone.

8. The method of claim 1 wherein said gas comprising alkanes comprises $C_2$-$C_5$ alkanes.

9. A method for dehydrogenating alkanes to form the corresponding olefins which comprises contacting a gas comprising said alkanes at a temperature within the range of about 500° to 1000° C. with a solid consisting essentially of:
   (a) at least one reducible oxide of Sb,
   (b) at least one promoter selected from the group consisting of alkali metals and compounds thereof, and
   (c) a support consisting essentially of at least one member of the group consisting of oxides of alkaline earth metals,
said contacting being conducted in the substantial absence of catalytically effective Ni, Rh, Pd, Ag, Os, Ir, Pt and Au.

10. The method of claim 9 wherein the support is magnesia.

11. The method of claim 9 wherein the promoter is selected from the group consisting of sodium, sodium compounds and mixtures thereof.

12. The method of claim 9 wherein the promoter is selected from the group consisting of potassium, potassium compounds and mixtures thereof.

13. The method of claim 9 wherein the promoter is selected from the group consisting of lithium, lithium compounds and mixtures thereof.

14. The method of claim 9 wherein the solid contains a stabilizing amount of phosphorous.

15. The method of claim 9 wherein the gas comprising alkanes and the solid comprising at least one reducible oxide of Sb are contacted in a first zone to form olefins corresponding to said alkanes, coproduct water, and solids comprising a reduced oxide of Sb; said olefins are recovered; said olefins comprising a reduced oxide of Sb are at least periodically contacted with an oxygen-containing gas in a second zone to produce a solid comprising a reducible oxide of Sb; and returning said solid comprising a reducible oxide of Sb from the second zone to the first zone.

16. The method of claim 9 wherein said gas comprising alkanes comprises $C_2$-$C_5$ alkanes.

17. A method for dehydrogenating alkanes to form the corresponding olefins which comprises contacting a gas comprising said alkanes at a temperature within the range of about 500° to 850° C. with a solid consisting essentially of:
   (a) at least one reducible oxide of Bi
   (b) at least one promoter selected form the group consisting of alkali metals and compounds thereof, and
   (c) a support consisting essentially of at least one member of the group consisting of oxides of alkaline earth metals,
said contacting being conducted in the substantial absence of catalytically effective Ni, Rh, Pd, Ag, Os, Ir, Pt and Au.

18. The method of claim 17 wherein the support is magnesia.

19. The method of claim 17 wherein the promoter is selected from the group consisting of sodium, sodium compounds and mixtures thereof.

20. The method of claim 17 wherein the promoter is selected from the group consisting of potassium, potassium compounds and mixtures thereof.

21. The method of claim 17 wherein the promoter is selected from the group consisting of lithium, lithium compounds and mixtures thereof.

22. The method of claim 17 wherein the solid contains a stabilizing amount of phosphorous.

23. The method of claim 17 wherein the gas comprising alkanes and the solid comprising at least one reducible oxide of Bi are contacted in a first zone to form olefins corresponding to said alkanes, coproduct water, and solids comprising a reduced oxide of Bi; said olefins are recovered; said olefins comprising a reduced oxide of Bi are at least periodically contacted with an oxygen-containing gas in a second zone to produce a solid comprising a reducible oxide of Bi; and returning said solid comprising a reducible oxide of Bi from the second zone to the first zone.

24. The method of claim 17 wherein said gas comprising alkanes comprises $C_2$–$C_5$.

* * * * *